United States Patent

Loftus (10) Patent No.: US 12,121,277 B2
(45) Date of Patent: *Oct. 22, 2024

(54) METHODS OF TREATING SACRAL INSUFFICIENCY FRACTURES AND DEVICES FOR PERFORMING SAME

(71) Applicant: Thomas Stuart Loftus, Johnson City, TX (US)

(72) Inventor: Thomas Stuart Loftus, Johnson City, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/482,218

(22) Filed: Oct. 6, 2023

(65) Prior Publication Data

US 2024/0032975 A1    Feb. 1, 2024

Related U.S. Application Data

(63) Continuation of application No. 17/744,510, filed on May 13, 2022, now Pat. No. 11,813,009.

(51) Int. Cl.
| | |
|---|---|
| *A61B 17/88* | (2006.01) |
| *A61B 34/20* | (2016.01) |
| *A61B 17/56* | (2006.01) |
| *A61B 90/00* | (2016.01) |
| *A61F 2/30* | (2006.01) |

(52) U.S. Cl.
CPC ...... *A61B 17/8811* (2013.01); *A61B 17/8819* (2013.01); *A61B 34/20* (2016.02); *A61B 2017/564* (2013.01); *A61B 2090/376* (2016.02); *A61F 2002/30995* (2013.01)

(58) Field of Classification Search
CPC . A61B 17/88; A61B 17/8802; A61B 17/8805; A61B 17/8816; A61B 17/8819; A61B 17/883; A61B 17/885
See application file for complete search history.

(56) References Cited

U.S. PATENT DOCUMENTS

| | | |
|---|---|---|
| 6,575,919 B1 | 6/2003 | Reiley et al. |
| 9,788,862 B2 | 10/2017 | Mootien et al. |
| 9,974,573 B2 * | 5/2018 | Schell ............... A61B 17/1671 |
| 10,064,670 B2 | 9/2018 | Mootien et al. |

(Continued)

OTHER PUBLICATIONS

Hatgis J, Granville M, Jacobson R E, et al. (Feb. 2, 2017) Sacral Insufficiency Fractures: Recognition and Treatment in Patients with Concurrent Lumbar Vertebral Compression Fractures. Cureus 9(2): e1008. DOI 10.7759/cureus.1008.

Tian et al., Fluoroscopy-Guided Percutaneous Sacroplasty for Painful Metastases at the Sacral Ala, Journal of Pain Research 2020:13 151-156.

(Continued)

*Primary Examiner* — Anu Ramana
(74) *Attorney, Agent, or Firm* — David O. Simmons; IVC Patent Agency (57) ABSTRACT

A method for treatment of a sacral insufficiency fracture comprises a plurality of steps. A step is performed for placing an access device within a patient. Such placing of the access device includes causing a distal end portion of the access device to traverse through a sacroiliac joint of the patient and to traverse into the patient's sacrum until the distal end portion of the access device is within a region of the sacrum where a sacral insufficiency fracture is located. Thereafter, a step is performed for delivering bonding material though a portion of the access device into the sacrum at the region thereof where the sacral insufficiency fracture is located.

20 Claims, 8 Drawing Sheets

(56) References Cited

U.S. PATENT DOCUMENTS

| | | |
|---|---|---|
| 10,492,688 B2 | 12/2019 | Donner et al. |
| 10,603,055 B2 | 3/2020 | Donner et al. |
| 2007/0282345 A1 | 12/2007 | Yedlicka et al. |
| 2007/0282447 A1 | 12/2007 | Yedlicka et al. |
| 2008/0140082 A1 | 6/2008 | Erdem et al. |
| 2009/0234399 A1 | 9/2009 | Cragg |
| 2012/0022568 A1 | 1/2012 | Koblish et al. |
| 2012/0113238 A1 | 5/2012 | Yamamoto et al. |
| 2016/0038631 A1 | 2/2016 | Persson et al. |
| 2018/0104071 A1* | 4/2018 | Reckling .......... A61B 6/505 |
| 2019/0083271 A1 | 3/2019 | Donner et al. |
| 2019/0209011 A1 | 7/2019 | Donner et al. |
| 2019/0343640 A1 | 11/2019 | Donner et al. |
| 2021/0113239 A1 | 4/2021 | Donovan |

OTHER PUBLICATIONS

Butler et al., Percutaneous Sacroplasty for the Treatment of Sacral Insufficiency Fractures, AJR 2005; 184:1956-1959.

Kao et al., Combination of long- and short-axis alar sacroplasty techniques under fluoroscopic guidance for osteoporotic sacral insufficiency fracture, Journal of Orthopaedic Surgery and Research (2021) 16:269.

Nicholson et al., Single-Needle Lateral Sacroplasty Technique, AJNR Am J Neuroradiol (2018) 1-4.

Sun et l., Three-Dimensional C-Arm Computer Tomography Reformation Combined With Fluoroscopic-Guided Sacroplasty for Sacral Metastases, Springer, Support Care Cancer (2012), 2083-2088.

* cited by examiner

METHODS OF TREATING SACRAL INSUFFICIENCY FRACTURES AND DEVICES FOR PERFORMING SAME

CROSS REFERENCE TO RELATED APPLICATIONS

This continuation patent application claims priority from co-pending U.S. Non-Provisional patent application having Ser. No. 17/744,510 filed May 13, 2022 entitled "METHODS OF TREATING SACRAL INSUFFICIENCY FRACTURES AND DEVICES FOR PERFORMING SAME", which has a common applicant herewith and is being incorporated herein in its entirety by reference.

FIELD OF THE DISCLOSURE

The disclosures made herein relate generally to treatment techniques for spinal and pelvic ailments and, more particularly, to methods of treating sacral insufficiency fractures and devices for performing same.

BACKGROUND

Sacral insufficiency fractures generally involve a non-displaced fracture of the sacrum. They are typically very painful, causing site-specific pain and leading to significant debility in patients. The underlying cause for such fractures is poor bone quality such as from a result of osteoporosis or osteopenia. Accordingly, sacral insufficiency fractures are most often seen in the elderly population. Although this type of fracture is often the result of trauma, lifting, or excessive activity, they also may occur with no clear inciting event.

Non-surgical treatment for sacral insufficiency fractures involves prolonged bedrest, with the understanding that the fractures will eventually heal on their own. Unfortunately, prolonged bedrest has well-documented negative effects, including complications such as blood clots, muscle wasting, deconditioning, etc. An intermittently-used surgical treatment for sacral insufficiency fractures has been sacroplasty, which involves a radiologist performing a procedural variation of the more widely used vertebroplasty or kyphoplasty procedures in a CT-guided setting. Vertebroplasty and kyphoplasty procedures are used to treat vertebral body fractures. In this regard, sacroplasty generally requires significant planning which has been known to delay treatment, make it logistically/financially unviable, or both.

Therefore, methods of surgical treatment for sacral insufficiency fractures that overcomes drawbacks associated with conventional surgical and non-surgical treatments would be advantageous, desirable and useful.

SUMMARY OF THE DISCLOSURE

Embodiments of the disclosures made herein are directed to methods of surgical treatment for sacral insufficiency fractures and devices used in such methods. Beneficially, these treatment methods are more attainable for surgeons already performing sacroiliac joint (SJ) fusions because it employs familiar radiological landmarks and because it is a more efficient technique for performing sacroplasty. Thus, because treatment methods in accordance with the disclosures made herein utilize only fluoroscopy and not a computerized tomography (CT) scanner or other type of imaging technology, the ability to schedule procedures for such treatment methods in an operating room (OR) or a procedure suite are much more cost-effective and are logistically much simpler—i.e., does not require services of a radiologist and CT scanner. The end result is that such treatment methods will allow more readily-available sacral fracture treatment for patients and ultimately allow faster alleviation of suffering and lead to better outcomes both short-term and long-term. Accordingly, methods of surgical treatment for sacral insufficiency fractures in accordance with embodiments of the disclosures made herein advantageously overcome drawbacks associated with conventional surgical and non-surgical treatments.

In one or more embodiments of the disclosures made herein, a method for treatment of a sacral insufficiency fracture comprises a plurality of steps. A step is performed for placing an access device within a patient. Such placing of the access device includes causing a distal end portion of the access device to traverse through a sacroiliac joint of the patient and to traverse into the patient's sacrum until the distal end portion of the access device is within a region of the sacrum where a sacral insufficiency fracture is located. Thereafter, a step is performed for delivering bonding material though a portion of the access device into the sacrum at the region thereof where the sacral insufficiency fracture is located.

In one or more embodiments of the disclosures made herein, an access device adapted for treatment of a skeletal fracture comprises a trocar having a central passage and a stylet having a portion thereof deposed within a central passage of the trocar. The distal end portion of the access device includes a distal end portion of the trocar. The stylet includes engagement structures that engage mating engagement structures of the trocar for maintaining the stylet in a fixed axial position within the central passage of the trocar when the mating engagement structures are in an engaged configuration and enabling the stylet to be removed from within the central passage of the trocar when the mating engagement structures are in a disengaged configuration.

In one or more embodiments, placing the access device is performed using only fluoroscopy for visualizing guidance of the access device.

In one or more embodiments, the method for treatment of the sacral insufficiency fracture further comprises identifying an intended entry point for the access device.

In one or more embodiments, identifying the intended entry point includes determining a dorsal sacral line and a superior alar line in regard to the patient's pelvic anatomy.

In one or more embodiments, the intended entry point is approximately 2-4 centimeters inferior to the dorsal sacral line and approximately 2-4 centimeters posterior to the superior alar line.

In one or more embodiments, delivering the bonding material includes attaching a bonding material delivery device to a trocar of the access device and using the bonding material delivery device to inject the bonding material into the region of the sacrum where the sacral insufficiency fracture is located.

In one or more embodiments, the access device includes mating engagement structures that maintaining the stylet in a fixed axial position within the central passage of the trocar when the mating engagement structures are in an engaged configuration and enabling the stylet to be removed from within the central passage of the trocar when the mating engagement structures are in a disengaged configuration.

In one or more embodiments, placing the access device includes maintaining the trocar and stylet in the engaged configuration and removing the stylet from within the central passage of the trocar includes manipulating the trocar and stylet to be in the disengaged configuration.

In one or more embodiments, the access device includes a trocar and a stylet having a portion thereof deposed within a central passage of the trocar, the distal end portion of the access device includes a distal end portion of the trocar and delivering the bonding material includes removing the stylet from within the central passage of the trocar after placing an access device and attaching a bonding material delivery device to a proximate end portion of the trocar removing the stylet from within the central passage of the trocar.

In one or more embodiments, the method for treatment of the sacral insufficiency fracture further comprises inserting the stylet back into the central passage after injecting the bonding material and removing the access device from the patient after the bonding material has fully or partially cured.

In one or more embodiments, the method for treatment of the sacral insufficiency fracture further comprises urging the distal end portion of the access device into fixed engagement with an ilium wing of the patient's pelvic anatomy and, in response to attaining fixed engagement with the ilium wing of the patient's pelvic anatomy, assessing at least one of inlet and outlet fluoroscopic views of the patient's pelvic anatomy to verify an intended trajectory of the distal end portion of the access device, and while viewing the distal end portion of the access device under live fluoroscopy, further urging the distal end portion of the access device until the distal end portion of the access device traverses the sacroiliac joint and protrudes into the sacrum.

In one or more embodiments, the access device adapted for treatment of a skeletal fracture further comprises an adaptor configured for enabling attachment to the bonding material delivery device to the trocar to allow the bonding material to be delivered to an operative site through the central passage of the trocar.

In one or more embodiments, the adapter is a threaded mounting body integral with a handle of the trocar.

These and other objects, embodiments, advantages and/or distinctions of the present invention will become readily apparent upon further review of the following specification, associated drawings and appended claims.

DETAILED DESCRIPTION

In general, embodiments of the disclosures made herein are directed to methods of surgical treatment for sacral insufficiency (SI) fractures and devices used in such methods. Because treatment methods in accordance with embodiments of the disclosures made herein preferably utilize only fluoroscopy, scheduling procedures for such treatment methods in an operating room (OR) or a procedure suite may be much more cost-effective and logistically much simpler. Accordingly, treatment methods in accordance with embodiments of the disclosures made herein allow for more readily-available sacral fracture treatment for patients and ultimately allow faster alleviation of suffering and lead to better outcomes both short-term and long-term.

Figure 1:
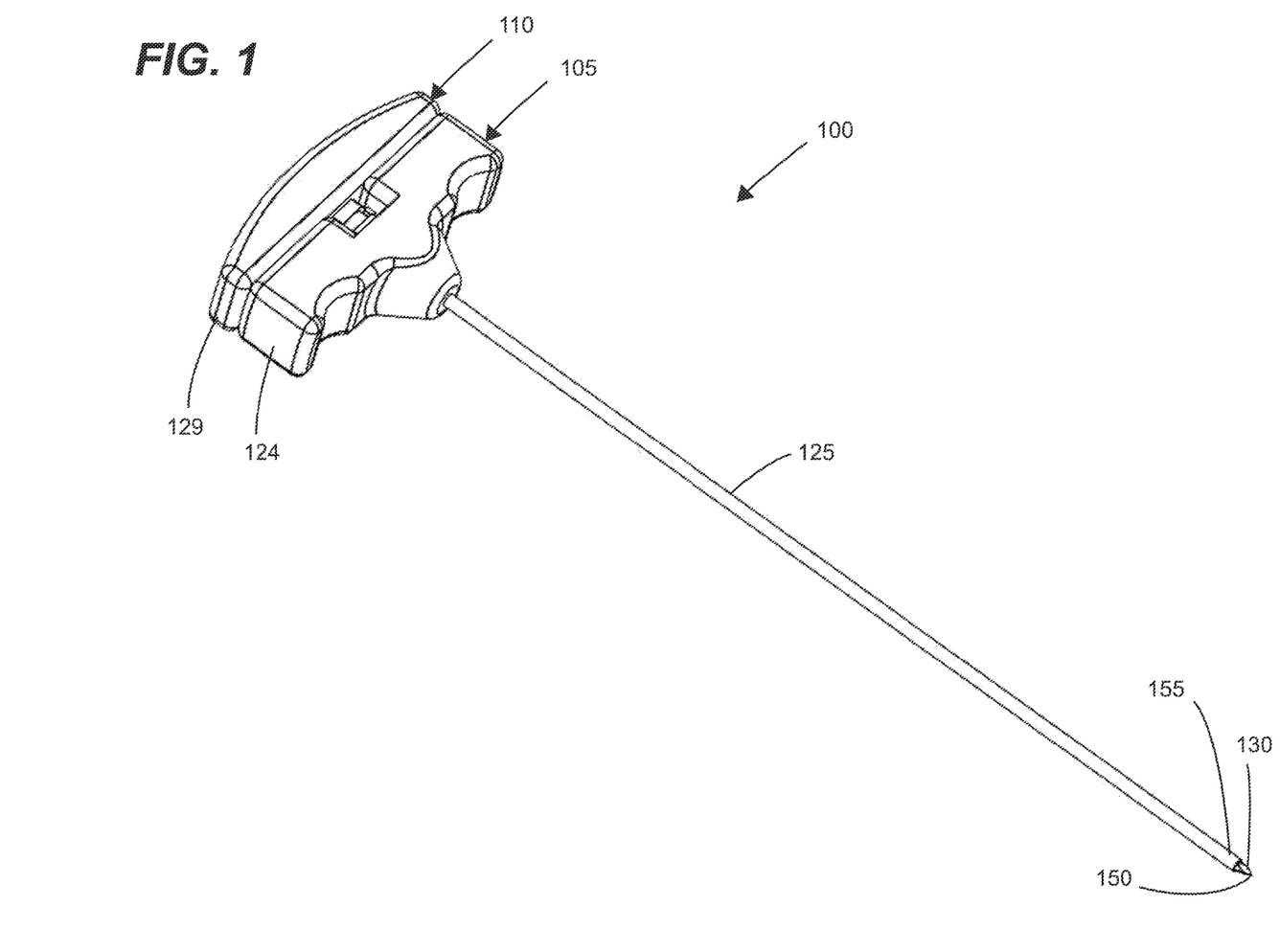
FIG. 1 is a perspective view showing an access device in accordance with one or more embodiment of the disclosures made herein.
Figure 2:
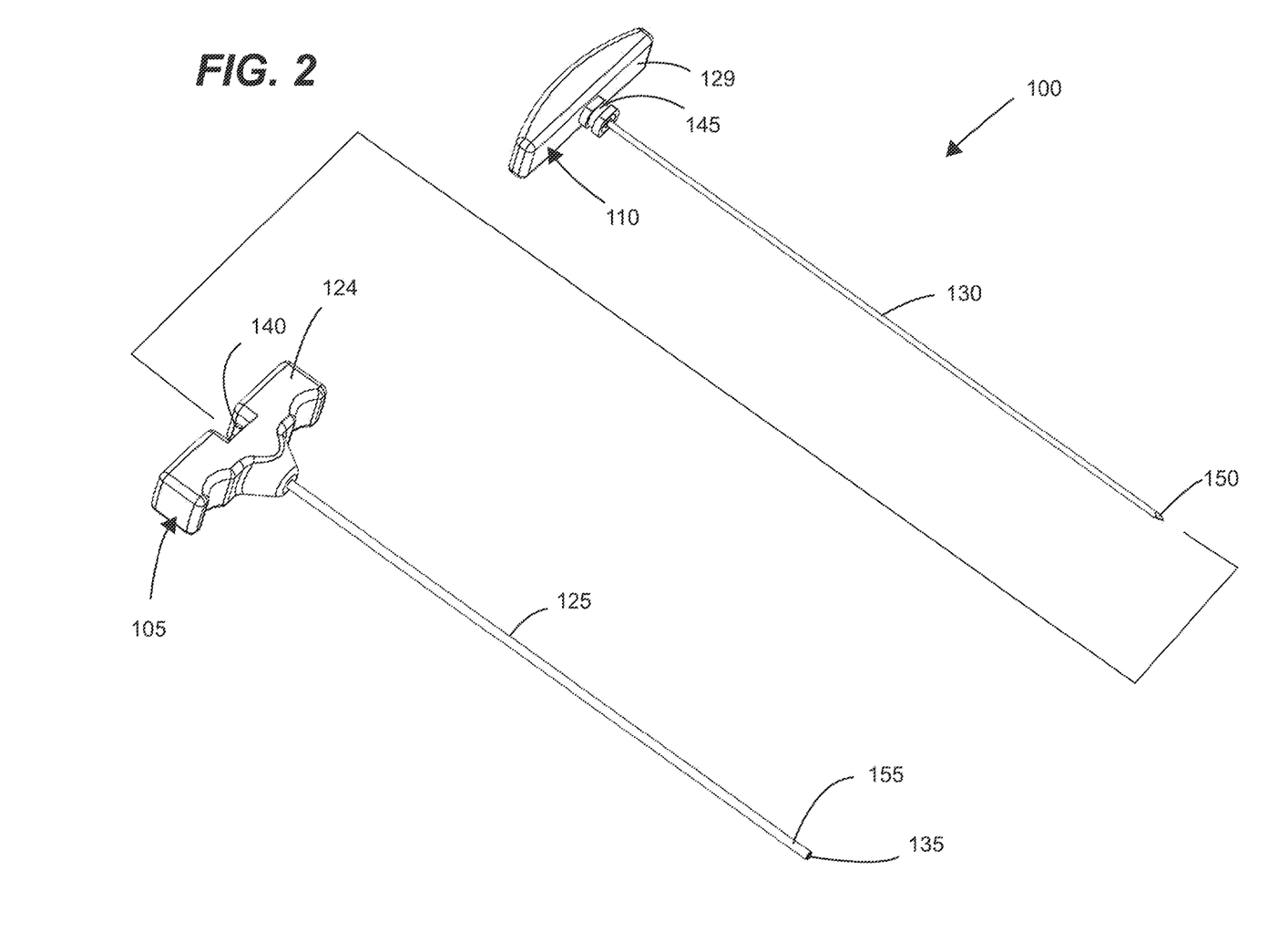
FIG. 2 is an exploded view of the access device of FIG. 1.

Treatment methods in accordance with embodiments of the disclosures made herein may involve use of an access device 100 comprising a trocar unit 105 and a stylet unit 110, as shown in FIGS. 1-6. The trocar unit 105 has a trocar handle 124 and a trocar 125 attached to the trocar handle 124. The stylet unit 110 has a stylet handle 129 and a stylet 130 attached to stylet handle 129. A central passage 135 extends through the trocar handle 124 and the trocar 125. The stylet 130 is engageable within the central passage 135. Preferably, the stylet 130 has a length to where a distal end portion 150 of the stylet 130 extends beyond a distal end portion 155 of the trocar 125 when the trocar unit 105 and the stylet unit 110 are engaged with each other, as shown in FIG. 1). Although similar in design to vertebroplasty devices, the trocar unit 105 is designed to allow access to deeper elements of the sacrum and better control of the trocar 125 at deeper depths. For example, in preferred embodiments, the trocar 125 may be about an 11 gauge in size with a length of about 9 inches.

Figure 3:
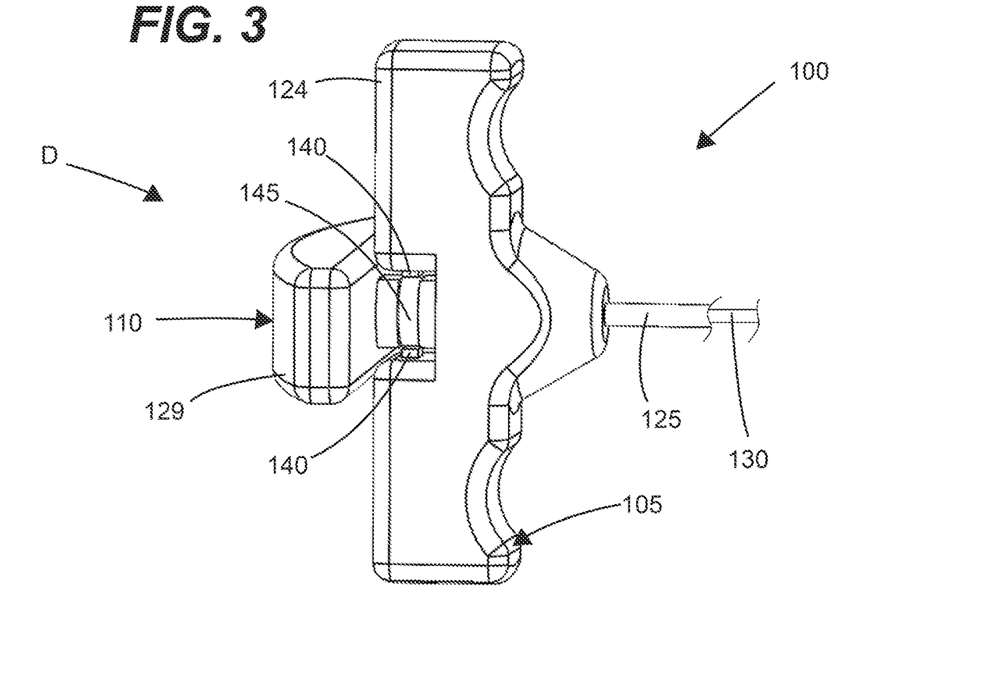
FIG. 3 is a partial view of the access device of FIG. 1, where a stylet unit (i.e., stylet and attached handle) is in a release configuration relative to a trocar unit (i.e., a trocar and attached handle)
Figure 4:
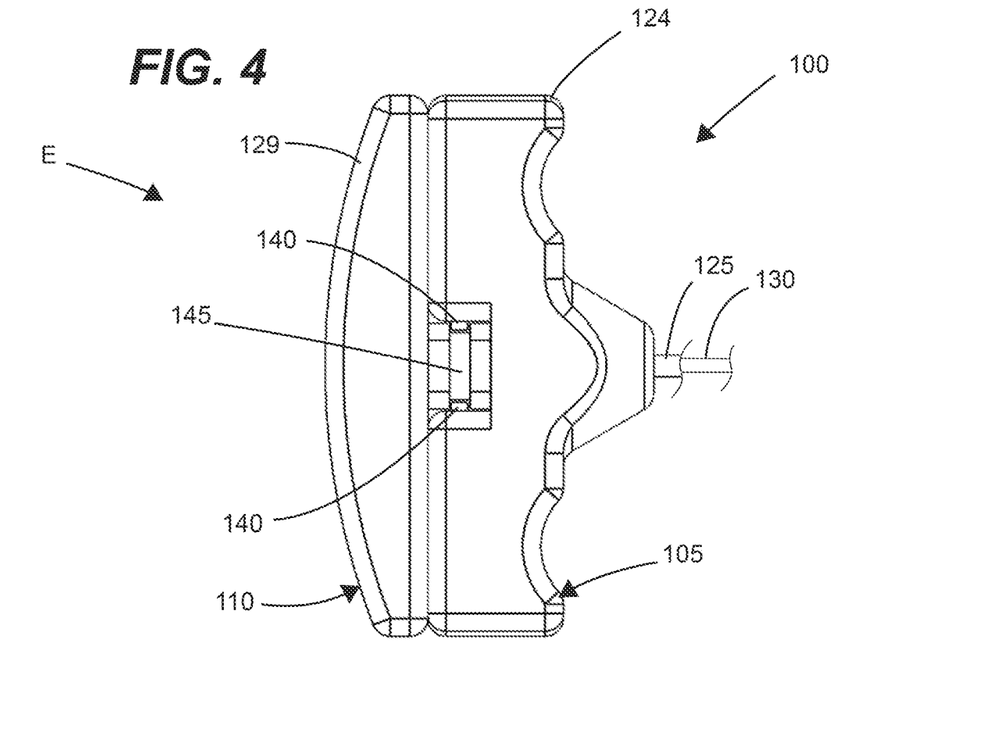
FIG. 4 is a partial view of the access device of FIG. 1, where the stylet unit is in an engaged configuration relative to the trocar unit.
Figures 5, 6:
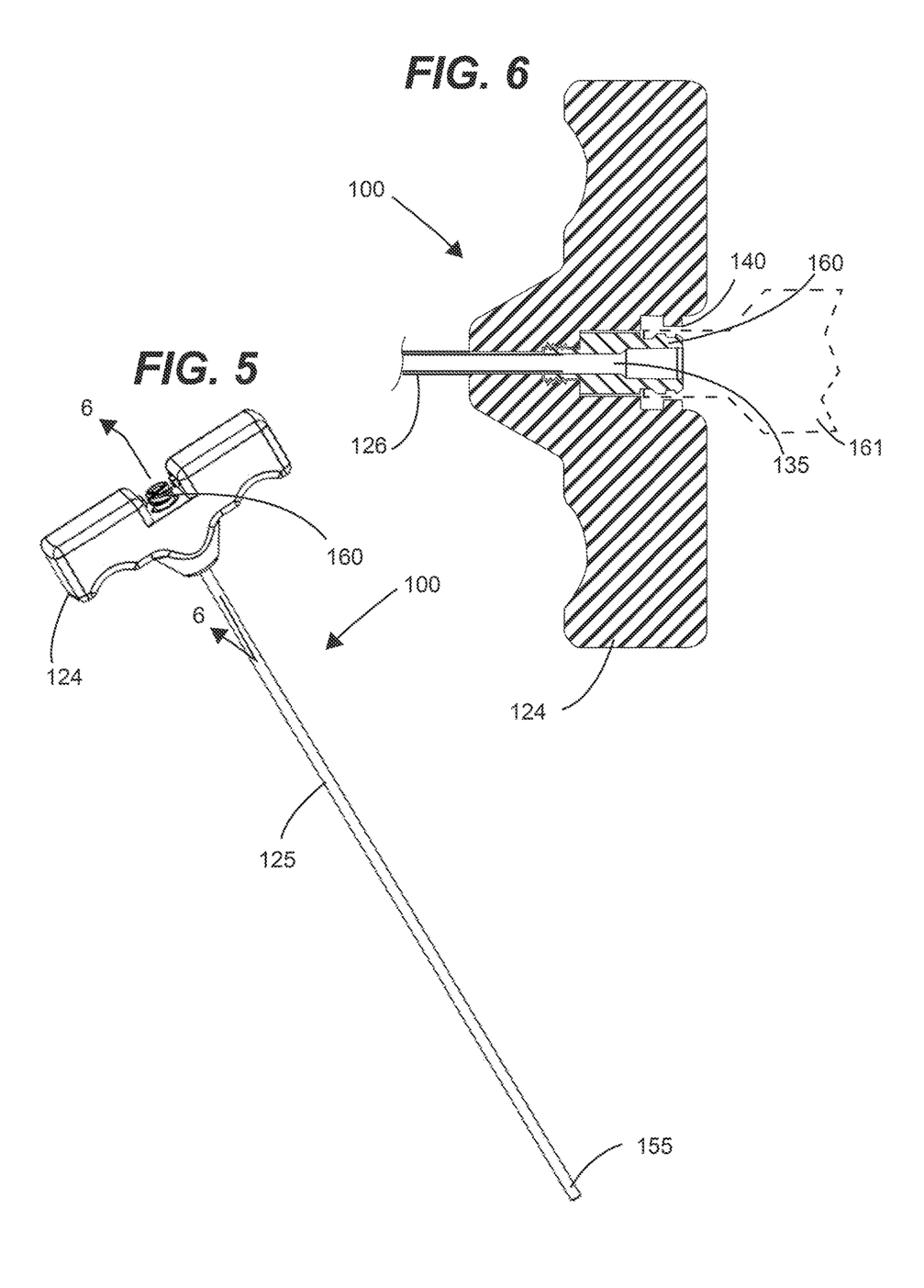
FIG. 5 is a perspective view of the trocar unit.
FIG. 6 is a cross-sectional view taken along the line 6-6 in FIG. 5.

The trocar handle 124 and the stylet handle 129 may be jointly configured to selectively allow the trocar unit 105 and the stylet unit 110 to be adjoined with each other (e.g., for inhibiting unrestricted axial displacement of the stylet 125 relative to the trocar unit 105) and to be separated from each other. For example, as best shown in FIGS. 3, 4 and 6, the trocar handle 124 may have one or more stylet engaging elements 140 (e.g., protruding members) that may be selectively engage with one or more trocar engaging elements 145 (e.g., a recess or channel) of the stylet handle 129. In this respect, the stylet engaging elements 140 are engagement structures of the trocar 125 and the trocar engaging elements 145 are engagement structures of the stylet 130. When the trocar handle 124 is in a disengaged configuration D relative to the stylet handle 129, the one or more stylet engaging elements 140 are disengaged from the one or more trocar engaging elements 145 (i.e., the mating engagement members of the trocar 125 and the stylet 130 are disengaged from each other), thereby enabling the trocar unit 105 and the stylet unit 110 to be selectively adjoined with and separated from each other. When the trocar handle 124 is in an engaged configuration E relative to the stylet handle 129, the one or more stylet engaging elements 140 are engaged with the one or more trocar engaging elements 145 (i.e., the mating engagement members of the trocar 125 and the stylet 130 are engaged with each other), thereby enabling inhibiting unrestricted axial displacement of the stylet 125 relative to the trocar unit 105.

Preferably, as best shown in FIGS. 5 and 6, the trocar unit 105 includes an adaptor 160 (e.g., a threaded mounting body such as a Leuer Lock). The adaptor 160 provides for attachment to a bonding material delivery device 161 such as a syringe (e.g., directly or via a piece of tubing). Through such attachment, bonding material (e.g., cement, adhesive or the like) may be dispensed from the bonding material delivery device 151 through the trocar unit 105 to a site of a sacral insufficiency fracture.

Figure 7:
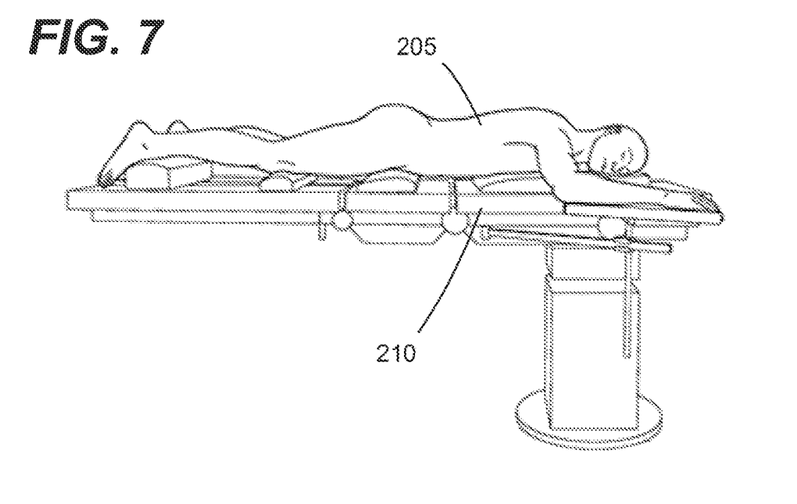
FIG. 7 is an illustrative view showing a patient in a prone position on an operating table.

Presented now is one specific embodiment of a SI fracture treatment method in accordance with the disclosures made herein (i.e., method 200), which utilizes the access device 100. The method 200 begins with the SI fracture patient 205 being placed in a prone position on an operating table 210, as shown in FIG. 7, and is then administered anesthesia. Preferably, the operating table 210 is a radiolucent style of table—e.g., a Jackson radiolucent table.

Figure 8:
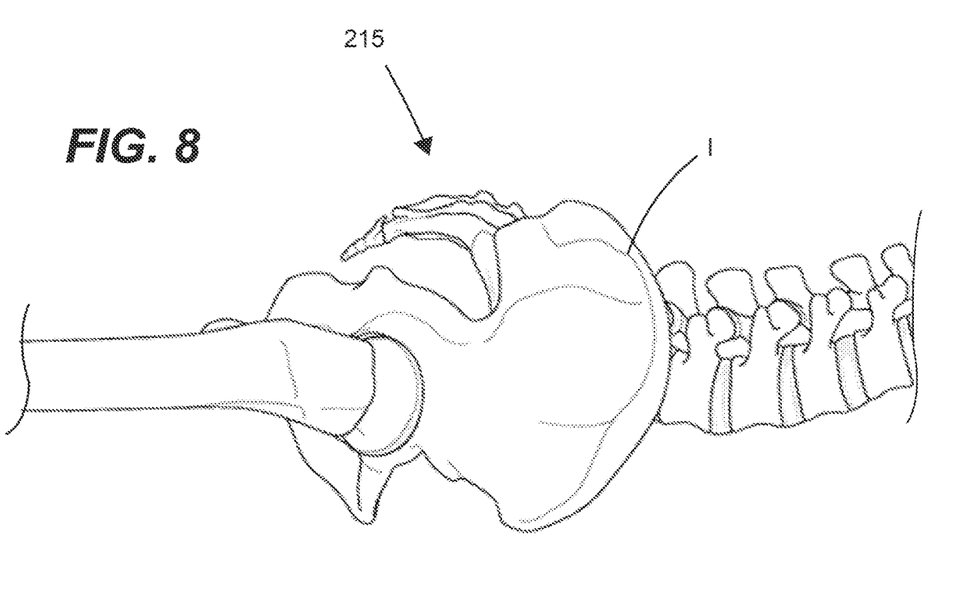
FIG. 8 is a lateral view of a pelvic portion of the patient's anatomy (i.e., pelvic anatomy)
Figure 9:
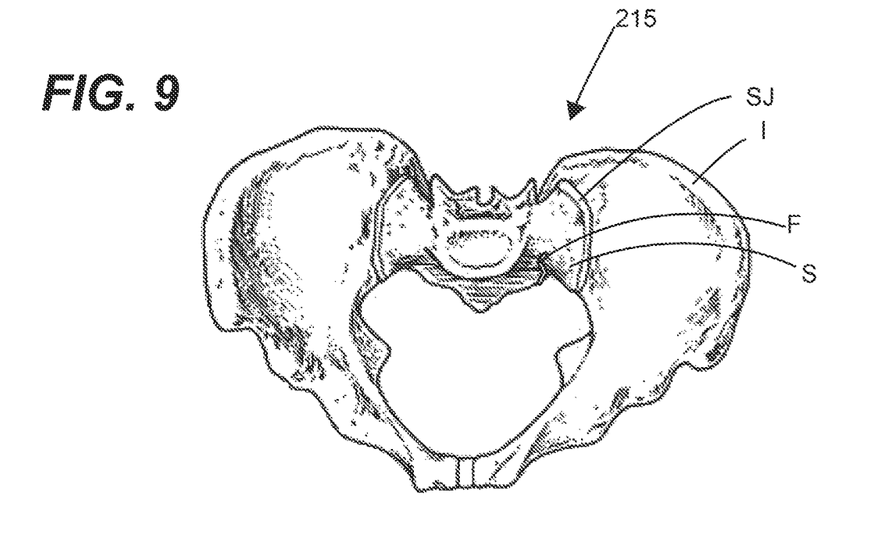
FIG. 9 is an inlet view of the pelvic portion of the patient's anatomy.
Figure 10:
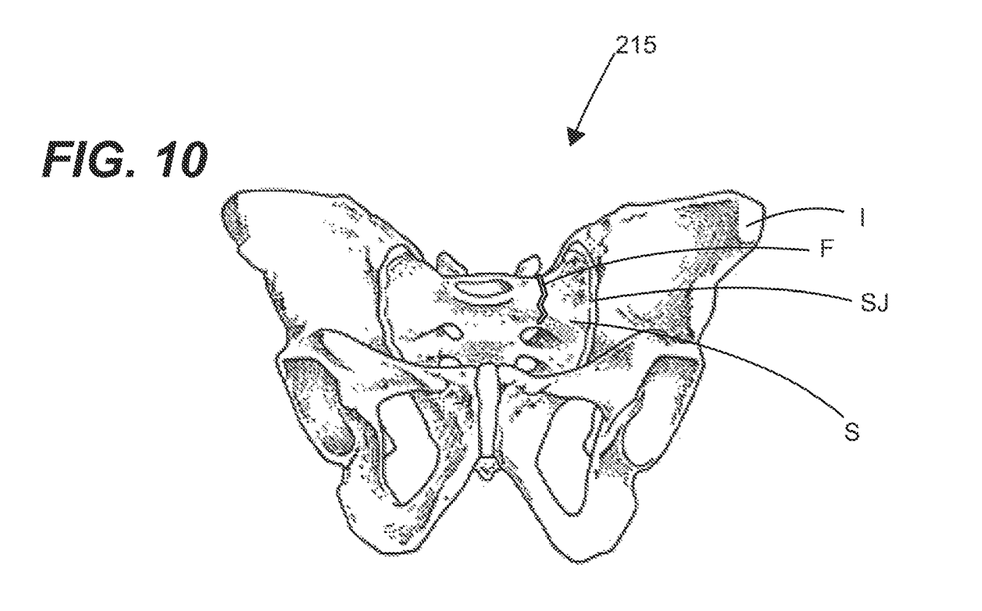
FIG. 10 is an outlet view of the pelvic portion of the patient's anatomy.
Figure 11:
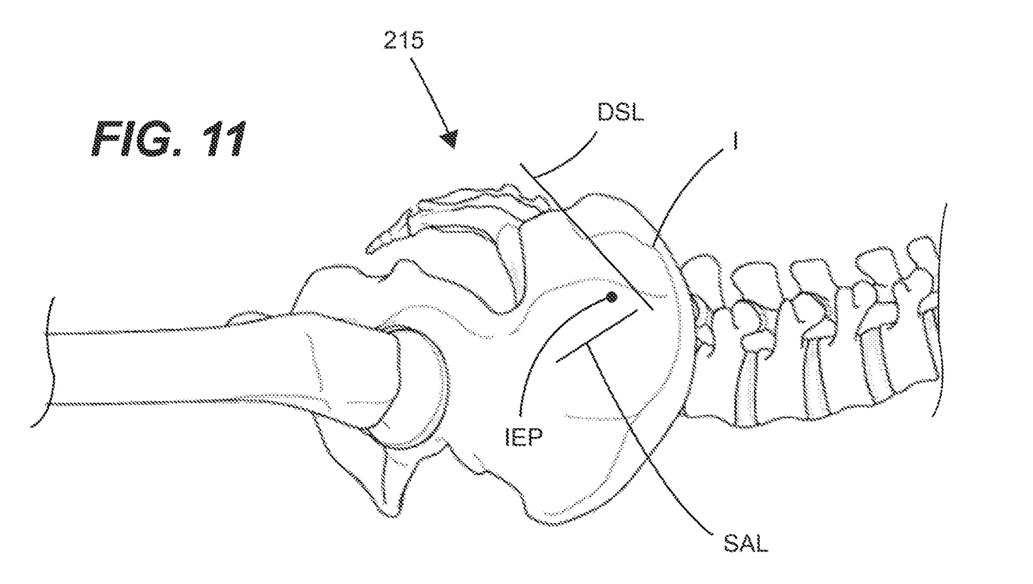
FIG. 11 is the lateral view of the pelvic portion of the patient's anatomy with access device entry point reference information shown.

A collection of images are taken of the patient's skeletal anatomy 215 in the pelvic region (i.e., pelvic anatomy) to aid in performing treatment of the SI fracture F (FIGS. 9 and 10). Such images are taken of an affected side of the sacrum to identify an intended entry point for insertion of the access device 100. Preferably, these views may include a lateral view (FIG. 8), an inlet view (FIG. 9), such as an AP view with 30 degree caudal angle, and an outlet view (FIG. 10), such as an AP view with 30 degree cranial angle). As shown in FIG. 11, a dorsal sacral line DSL and a superior alar line SAL in regard to the patient's skeletal anatomy are referenced for use during the surgical procedure (e.g., are marked ipsilaterally on the patient's skin at the lateral aspect of the buttock). The dorsal sacral line is comprised of the dorsal aspect of the five fused vertebrae that comprise the sacrum. In a true lateral projection radiographic image (i.e., fluoroscopy), the dense nature of this dorsal aspect of the sacrum forms a corresponding highly-visible line—i.e., represented by the dorsal sacral line DSL shown in FIG. 11. The superior alar line is formed by the superior edge of the alar wings that project horizontally from the sacrum bilaterally. In a true lateral radiographic image, the dense nature of the superior edges of each alar wing will align to form a corresponding highly-visible line—i.e., represented by the superior alar line SAL shown in FIG. 11. The dorsal sacral line and the superior alar line intersect, as shown, and they can be used to verify the surgeon has achieved a true lateral radiographic image and to perform required measurements for entry point targeting." The intended entry point IEP is then also similarly referenced at a location approximately 2-4 cm inferior to the dorsal sacral line DSL and 2-4 cm posterior to the superior alar line SAL. After the area surrounding the intended entry point is prepped and draped in standard sterile fashion. The intended entry point IEP may again be verified via fluoroscopy.

Figure 12:
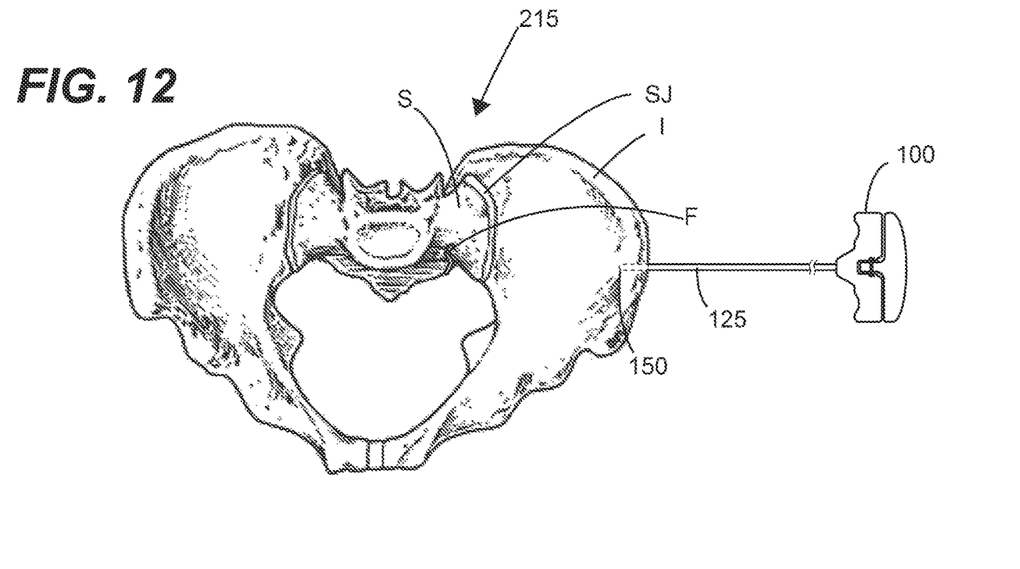
FIG. 12 is the inlet view of the pelvic portion of the patient's anatomy showing an SI fracture and an access device shown in a partially placed position.
Figure 13:
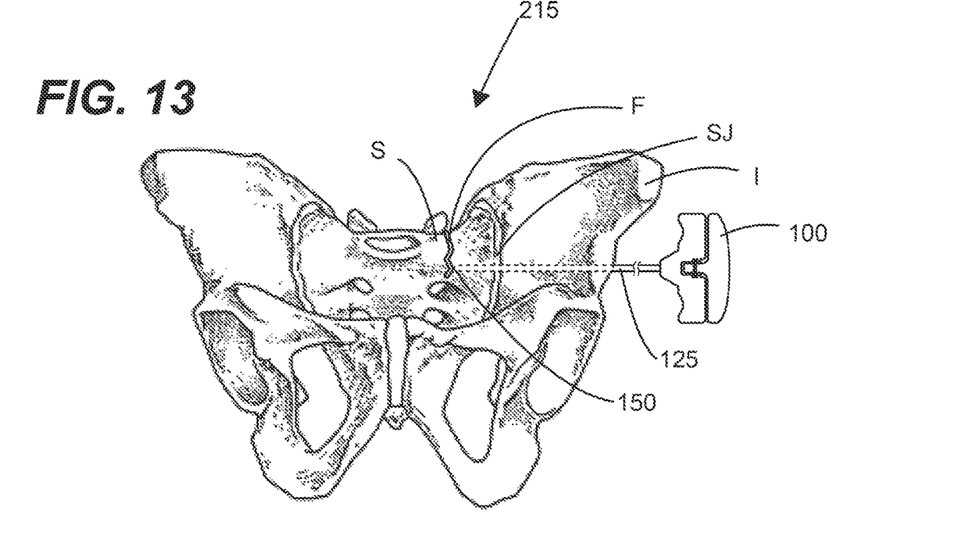
FIG. 13 is the outlet view of the pelvic portion of the patient's anatomy showing the SI fracture and the access device shown in a partially placed position.

Next, a puncture is made at the intended entry point IEP (e.g., with an 11 blade scalpel). Referring to FIGS. 12 and 13, lateral fluoroscopic guidance is then preferably used to begin placement of the access device 100 by passing a distal end portion 150 of the access device 100 through soft tissue of the patient toward the bone of the ilium wing I. As discussed above, preferred placement of the access device 100 is at the midportion between the dorsal sacral line DSL and the superior alar line SAL. Once the distal end portion 150 of the access device 100 is at the bone of the ilium wing I, the access device 100 is gently impacted (e.g., with a mallet) until good purchase between its distal end portion 150 and the ilium wing I is achieved. Additional inlet and outlet views are preferably obtained to verify appropriate trajectory of the access device 100 and to ensure avoidance of ventral breach of the sacrum S. While in outlet view, distal end portion 150 of the trocar unit 100 is gently urged farther until it traverses the sacroiliac joint SJ into the sacrum S. Continued urging of the distal end portion 150 of the access device 100 is carried out until it reaches a depth that approximately aligns with the S1 pedicle, which should be readily visualized. Repeat inlet and lateral views are preferably taken to ensure appropriate position of the distal end portion 150 of the access device 100 and to ensure absence of ventral or dorsal breach of the sacrum S. In this manner, the access device 100 is placed from a lateral access point lateral to the gluteus muscle using lateral/inlet/outlet fluoroscopy views in sequence while guiding the access device 100 medially across the ilium/alar wing into the sacrum S. This placement approach results in placement of the distal end portion 150 of the access device 100 being in the region of the noted SI fracture.

Once correct placement of the access device 100 relative to the bony confines of the sacrum S is verified (e.g., by 3 views of fluoroscopy—lateral, outlet and inlet), a bonding material (e.g., cement such as methylmethacrylate polymer) is injected through the central passage 135 of the trocar unit 105 under live fluoroscopy after removal of the stylet unit 110 from within the central passage 135. As filling of sacral fracture site begins, intermittent breaks in the bonding material delivery may be taken to obtain inlet and lateral fluoroscopic views to verify that none of the bonding material has exhibited extravasation beyond the sacral margins. Bonding material injection continues until visual confirmation of bonding material traversal of the SI fracture site indicated on pre-operative imaging has been achieved. Bonding material delivery is preferably performed under live fluoroscopy with intermittent images (e.g., lateral and inlet) to confirm absence of bonding material extravasation beyond the sacral confines. Additionally, the S1 foramen may be monitored (e.g., via outlet view) during injection to ensure no encroachment of the bonding material on the S1 foramen. Once adequate filling has been achieved, the stylet unit 110 is re-engaged with the trocar unit 105 to expel remaining cement preferably under live outlet fluoroscopy. The bonding material is allowed to sufficiently cure (e.g., approximately 1-2 minutes for methylmethacrylate polymer) and then the access device 100 is removed.

In one or more embodiments, a rotatory manual injector syringe (i.e., a bonding material delivery device) may be used to inject the bonding material. As discussed above, the bonding material the trocar unit 105 includes an adaptor 160 that provides for attachment to the bonding material delivery device 161 either directly or via a conduit (e.g., a piece of tubing). Prior to attachment of the bonding material delivery device to the trocar unit 105, the central passage 135 of the trocar unit 105 may be lightly filled with saline to allow air to be expelled (e.g., via elevated intravenous (IV) extension tubing). Optionally, a suitable visualization composition (e.g., Isovue 200M) may first be injected under live fluoroscopy to monitor an expected filling by the bonding material.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A method for treatment of a sacral insufficiency fracture, comprising:
inserting the distal end portion of an access device through an intended entry point of a patient and causing a distal end portion of the access device to traverse through a sacroiliac joint of the patient and to traverse into the patient's sacrum until the distal end portion of the access device is within a region of the sacrum where a sacral insufficiency fracture has been identified, wherein the intended entry point is approximately 2-4 centimeters inferior to the dorsal sacral line and approximately 2-4 centimeters posterior to the superior alar line; and
delivering bonding material into the sacrum though a central passage of the access device.

2. The method of claim 1 wherein said delivering of the bonding material includes temporarily pausing of said delivering and, during said temporarily pausing, performing fluoroscopic imaging for determining a proximity of delivered bonding material relative to sacral margins.

3. The method of claim 2 wherein:
the access device includes a trocar and a stylet having a portion thereof deposed within a central passage of the trocar;
the distal end portion of the access device includes a distal end portion of the trocar; and
said delivering includes removing the stylet from within the central passage of the trocar while the distal end portion of the trocar remains positioned within the region of the sacrum where the sacral insufficiency fracture is located and attaching a bonding material delivery device to a trocar of the access device for enabling delivery of bonding material from the bonding material delivery device into the sacrum through the central passage of the of the trocar.

4. The method of claim 3 further comprising:
inserting the stylet back into the central passage after injecting the bonding material during curing of the bonding material; and
removing the access device from the patient after the bonding material has one of fully and partially cured.

5. The method of claim 1 wherein said inserting is performed in combination with fluoroscopic imaging for visualizing trajectory of the distal end portion of the access device to ensure avoidance of ventral breach of the sacrum and for visualizing trajectory of the distal end portion of the access device to achieve traversal of the sacroiliac joint by the distal end portion of the access device and positioning of the distal end portion of the access device into the sacrum.

6. The method of claim 5 wherein said delivering of the bonding material includes temporarily pausing of said delivering and, during said temporarily pausing, performing fluoroscopic imaging for determining a proximity of delivered bonding material relative to sacral margins.

7. The method of claim 6 wherein:
the access device includes a trocar and a stylet having a portion thereof deposed within a central passage of the trocar;
the distal end portion of the access device includes a distal end portion of the trocar; and
said delivering includes removing the stylet from within the central passage of the trocar while the distal end portion of the trocar remains positioned within the region of the sacrum where the sacral insufficiency fracture is located and attaching a bonding material delivery device to a trocar of the access device for enabling delivery of bonding material from the bonding material delivery device into the sacrum through the central passage of the of the trocar.

8. The method of claim 7 further comprising:
inserting the stylet back into the central passage after injecting the bonding material during curing of the bonding material; and
removing the access device from the patient after the bonding material has one of fully and partially cured.

9. The method of claim 1 wherein:
the access device includes a trocar and a stylet having a portion thereof deposed within a central passage of the trocar;
the distal end portion of the access device includes a distal end portion of the trocar; and
said delivering includes removing the stylet from within the central passage of the trocar after inserting the access device and attaching a bonding material delivery device to a proximate end portion of the trocar.

10. The method of claim 1 wherein:
the access device includes a trocar and a stylet having a portion thereof deposed within a central passage of the trocar;
the distal end portion of the access device includes a distal end portion of the trocar; and
said delivering includes removing the stylet from within the central passage of the trocar while the distal end portion of the trocar remains positioned within the region of the sacrum where the sacral insufficiency fracture is located and attaching a bonding material delivery device to a trocar of the access device for enabling delivery of bonding material from the bonding material delivery device into the sacrum through the central passage of the of the trocar.

11. The method of claim 10, further comprising:
inserting the stylet back into the central passage after injecting the bonding material; and
removing the access device from the patient after the bonding material has one of fully and partially cured.

12. The method of claim 11 wherein:
the access device includes mating engagement structures that maintaining the stylet in a fixed axial position within the central passage of the trocar when the mating engagement structures are in an engaged configuration and enabling the stylet to be removing stylet from within the central passage of the trocar when the mating engagement structures are in a disengaged configuration;
inserting the access device includes maintaining the trocar and stylet in the engaged configuration; and
removing the stylet from within the central passage of the trocar includes manipulating the trocar and stylet to be in the disengaged configuration.

13. The method of claim 1 wherein inserting the access device includes:
urging the distal end portion of the access device into fixed engagement with an ilium wing of the patient's pelvic anatomy;

in response to attaining fixed engagement with the ilium wing of the patient's pelvic anatomy, assessing at least one of inlet and outlet fluoroscopic views of the patient's pelvic anatomy to verify an intended trajectory of the distal end portion of the access device; and while viewing the distal end portion of the access device under live fluoroscopy, further urging the distal end portion of the access device until the distal end portion of the access device traverses the sacroiliac joint and protrudes into the sacrum.

14. The method of claim 13 wherein said inserting includes using only fluoroscopy for visualizing guidance of the access device.

15. The method of claim 13 wherein:

the access device includes a trocar and a stylet having a portion thereof deposed within a central passage of the trocar;

the distal end portion of the access device includes a distal end portion of the trocar; and said delivering includes removing the stylet from within the central passage of the trocar while the distal end portion of the trocar remains positioned within the region of the sacrum where the sacral insufficiency fracture is located and attaching a bonding material delivery device to a trocar of the access device for enabling delivery of bonding material from the bonding material delivery device into the sacrum through the central passage of the of the trocar.

16. The method of claim 15, further comprising:

inserting the portion of the stylet back into the central passage after injecting the bonding material; and removing the access device from the patient after the bonding material has one of fully and partially cured.

17. The method of claim 15 wherein:

the access device includes mating engagement structures that maintaining the stylet in a fixed axial position within the central passage of the trocar when the mating engagement structures are in an engaged configuration and enabling the stylet to be removing the stylet from within the central passage of the trocar when the mating engagement structures are in a disengaged configuration;

inserting the access device includes maintaining the trocar and stylet in the engaged configuration; and removing the stylet from within the central passage of the trocar includes manipulating the trocar and stylet to be in the disengaged configuration.

18. The method of claim 17 wherein said inserting includes using only fluoroscopy for visualizing guidance of the access device.

19. The method of claim 13 wherein said inserting is performed in combination with fluoroscopic imaging for visualizing trajectory of the distal end portion of the access device to ensure avoidance of ventral breach of the sacrum and for visualizing trajectory of the distal end portion of the access device to achieve traversal of the sacroiliac joint by the distal end portion of the access device and positioning of the distal end portion of the access device into the sacrum.

20. The method of claim 19 wherein said delivering of the bonding material includes temporarily pausing of said delivering and, during said temporarily pausing, performing fluoroscopic imaging for determining a proximity of delivered bonding material relative to sacral margins.

* * * * *